United States Patent [19]
Urich et al.

[11] Patent Number: 6,117,151
[45] Date of Patent: Sep. 12, 2000

[54] EYE INCISION TEMPERATURE PROTECTING SLEEVE

[75] Inventors: Alex Urich, Mission Viejo; Michael Curtis, Lake Forest, both of Calif.

[73] Assignee: Circuit Tree Medical, Inc., Mission Viejo, Calif.

[21] Appl. No.: 09/186,993

[22] Filed: Nov. 5, 1998

[51] Int. Cl.[7] ............................................. A61B 17/32
[52] U.S. Cl. ................................. 606/169; 604/22
[58] Field of Search ............................ 606/169, 170, 606/171; 604/22

[56] References Cited

U.S. PATENT DOCUMENTS

| | | | |
|---|---|---|---|
| 4,808,154 | 2/1989 | Freeman . | |
| 4,983,160 | 1/1991 | Steppe et al. | 604/22 |
| 5,123,903 | 6/1992 | Quaid et al. | 604/22 |
| 5,282,786 | 2/1994 | Ureche . | |
| 5,354,265 | 10/1994 | Mackool . | |
| 5,380,274 | 1/1995 | Nita | 604/22 |
| 5,464,389 | 11/1995 | Stahl | 604/22 |
| 5,807,310 | 9/1998 | Hood . | |
| 5,817,099 | 10/1998 | Skolik et al. | 606/107 |

*Primary Examiner*—Michael Buiz
*Assistant Examiner*—Jonathan D. Goldberg
*Attorney, Agent, or Firm*—Irell & Manella LLP

[57] ABSTRACT

A sleeve for a medical handpiece. The sleeve has a flexible outer sleeve and a rigid inner sleeve that are both coupled to a case of the handpiece. Coupling the rigid inner sleeve to the case increases the effective stiffness of the inner sleeve. Increasing the effective stiffness of the rigid inner sleeve reduces the likelihood of contact between the inner sleeve and a tip of the handpiece even when non-symmetric forces are applied to the sleeve.

15 Claims, 2 Drawing Sheets

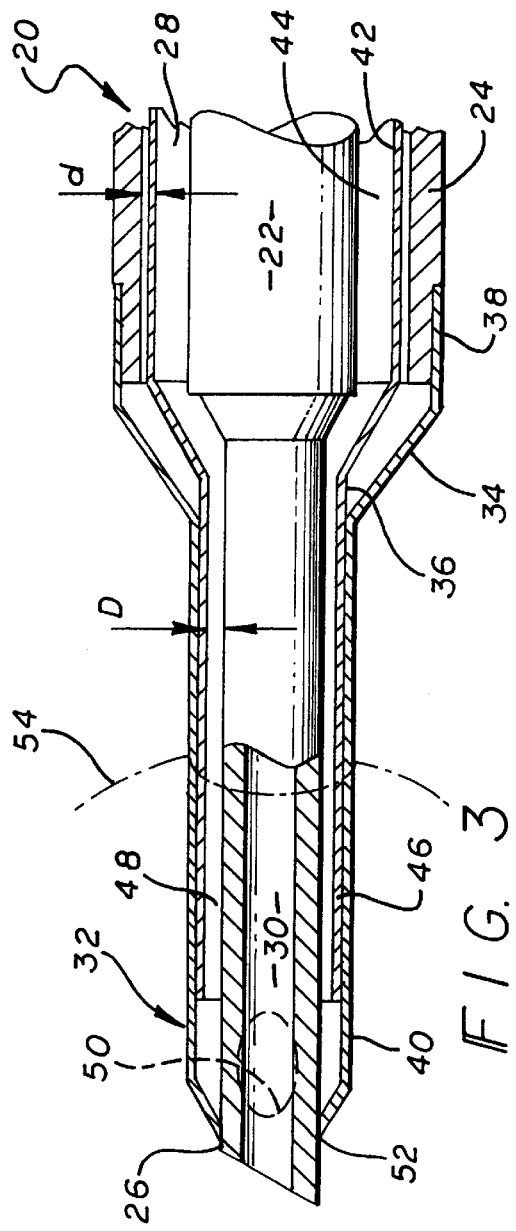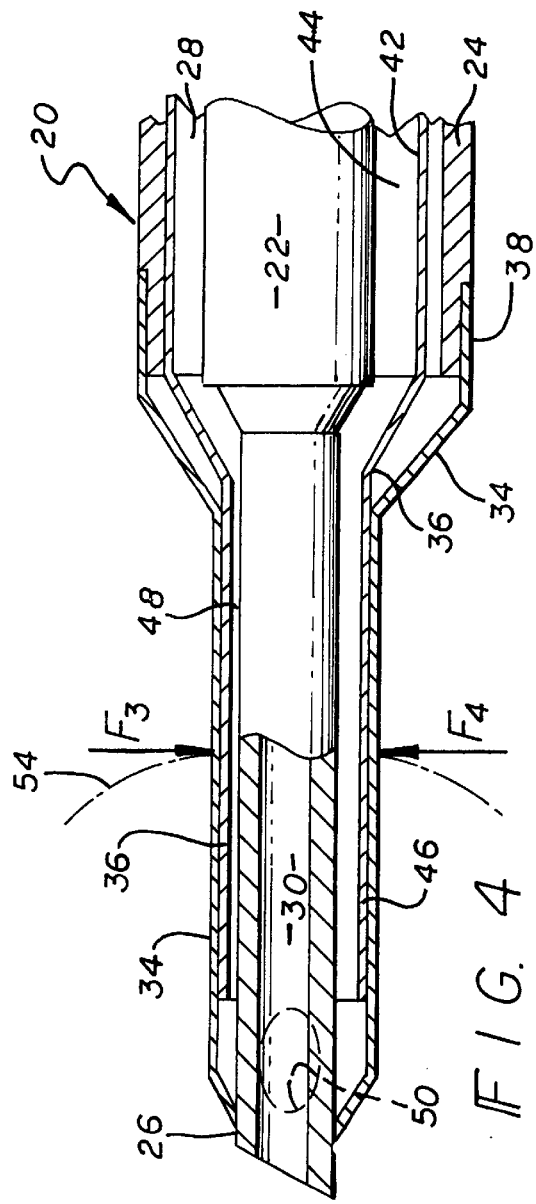

EYE INCISION TEMPERATURE PROTECTING SLEEVE

BACKGROUND OF THE INVENTION

1. Field of the Invention

The present invention relates to an irrigation sleeve for an ultrasonic medical handpiece.

2. Background Information

There has been developed a medical procedure commonly referred to as phacoemulsification ("phaco") that is performed to remove a cataracteous lens. A phaco procedure includes the steps of making an incision in the cornea and inserting a tip that is manipulated by a surgeon to break and remove the lens. The tip is typically driven by an ultrasonic device which imparts a vibratory energy to the lens. The tip extends from a handpiece that is coupled to an irrigation line and an aspiration system. The irrigation line provides an irrigation fluid to the anterior chamber of the cornea. The aspiration system pulls the irrigation fluid and emulsified lens from the cornea.

FIG. 1 shows a typical surgical instrument 1 used to perform phaco procedures. The surgical instrument 1 includes an outer irrigation sleeve 2 that is attached to an outer case 3 of the instrument 1. An ultrasonically driven tip 4 extends from the case 3 and through the sleeve 2. The vibrating tip 4 is used to emulsify the lens of a cornea 5.

The case 3 has an irrigation inlet port 6 that is connected to an irrigation line. The irrigation line provides an irrigation fluid to the instrument. The sleeve 2 has an irrigation port (not shown) that allows the irrigation fluid to flow into the eye. The sleeve 2 is separated from the tip 4 to create a channel 7 that allows irrigation fluid to flow from the inlet port 6 to the outlet port. The tip 4 has an aspiration channel that is connected to an aspiration system. The irrigation fluid and emulsified lens are drawn through the channel 8.

The irrigation fluid must be provided at a sufficient pressure and flowrate to maintain the interocular pressure of the cornea without damaging corneal tissue. It is desirable to provide an incision opening that is large enough to allow the tip 4 and sleeve 2 to be inserted into the cornea without allowing the irrigation fluid to leak back out of the anterior chamber. This requires making an incision that is approximately the same size as the outer diameter of the sleeve 2.

The cornea tissue about the incision may create frictional contact between the inner surface of the sleeve and the oscillating tip. The frictional contact between the sleeve and the tip creates heat. The heat may burn the endothelium tissue of the cornea. Damage to the endothelium is irreversible and may result in a permanent impairment of the patient's vision. It is therefore important to avoid corneal burning during a phaco procedure.

U.S. Pat. No. 5,354,265 issued to Mackool discloses an ultrasonic handpiece which has a flexible outer sleeve and a hard inner sleeve. The hard inner sleeve may reduce the amount of contact between the outer sleeve and the vibrating tip. The reduction in contact decreases the heat and probability of corneal burning. U.S. Pat. No. 5,282,786 issued to Ureche and U.S. Pat. No. 5,807,310 issued to Hood disclose irrigation sleeves that have bands which are constructed from a material such as TEFLON. The TEFLON sleeves have a stiffness that is greater than the stiffness of the rubber material. The TEFLON outer band may reduce the friction and corresponding heat generated between the cornea and the irrigation sleeve.

As shown in FIG. 2, the cornea may apply nonsymmetric forces $F_1$ and $F_2$ ($F_1 > F_2$) to the outer surface of the sleeve. The non-symmetric forces may push the inner sleeve into contact with the tip even with an inner sleeve or inner/outer bands disclosed in the prior art. The sleeve may make contact with the vibrating tip along the entire length of the tip to create a relatively large frictional area. Thus even with an inner sleeve or an inner/outer band the vibrating tip may still generate heat with the irrigation sleeve. It would be desirable to provide an irrigation sleeve that will reduce the likelihood of frictional contact between the sleeve and the vibrating tip.

SUMMARY OF THE INVENTION

One embodiment of the present invention is a sleeve for a medical handpiece. The sleeve has a flexible outer sleeve and a rigid inner sleeve that are both coupled to a case of the handpiece. Coupling the rigid inner sleeve to the case increases the effective stiffness of the inner sleeve. Increasing the effective stiffness of the rigid inner sleeve reduces the likelihood of contact between the inner sleeve and a tip of the handpiece even when non-symmetric forces are applied to the sleeve.

BRIEF DESCRIPTION OF THE DRAWINGS

FIG. 3 is a side sectional view of an ultrasonic handpiece of the present invention;

FIG. 4 is a side sectional view showing non-symmetric forces being applied to the irrigation sleeve of the handpiece.

DETAILED DESCRIPTION

Figure 1:
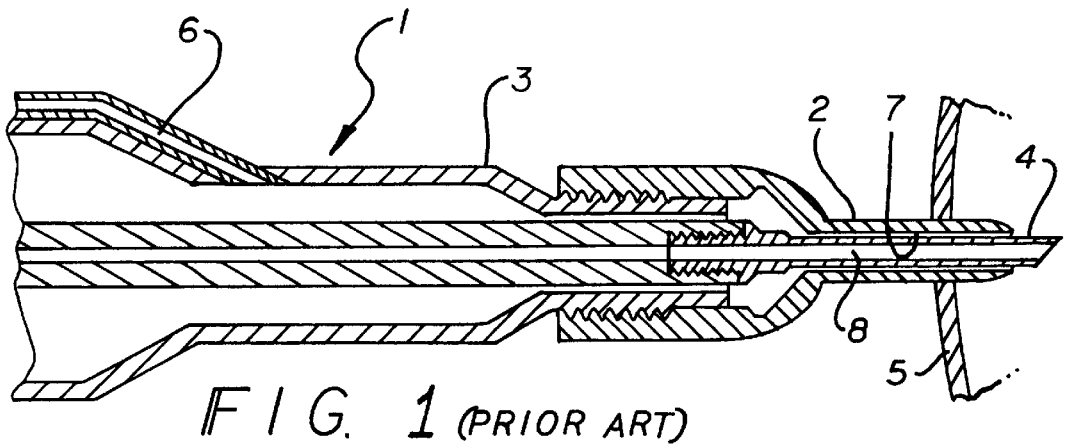
FIG. 1 is a side sectional view of an ultrasonic handpiece tip of the prior art.
Figure 2:
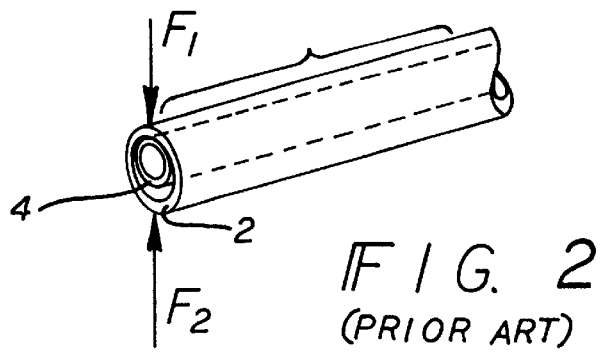
FIG. 2 is a front perspective view of an ultrasonic tip of the prior art.

Referring to the drawings more particularly by reference numbers, FIG. 3 shows an embodiment of an ultrasonic handpiece 20 of the present invention. The ultrasonic handpiece 20 may include an ultrasonic transducer 22 that is located within an outer case 24. A tip 26 is coupled to the transducer 22 and extends from the case 24. The transducer 22 is typically coupled to a power supply (not shown) that controls an oscillating motion of the tip 26.

The outer case 24 may have an irrigation channel 28 that is in fluid communication with a source of irrigation fluid (not shown). The tip 26 typically has an aspiration channel 30 that is coupled to a vacuum pump (not shown) as is known in the art.

The handpiece 20 may have an irrigation sleeve 32. The irrigation sleeve 32 may include a flexible outer sleeve 34 and a rigid inner sleeve 36. By way of example, the outer sleeve 34 may be constructed from a silicone rubber material and the inner sleeve 36 may be constructed from a hard plastic material such as a polysilifoam or a product sold under the tradename ULTEM. These materials have both relatively high melt temperatures to prevent melting in the event of frictional contact between the sleeve 36 and tip 26. These materials also have favorable frictional characteristics. In general the inner sleeve 36 will have a stiffness that is greater than the stiffness of the outer sleeve 34. In one embodiment, the inner sleeve may have a thickness of 0.003 inches.

The outer sleeve 34 may have a proximal portion 38 that is attached the case 24 and a distal portion 40 that extends along the length of the tip 26. The inner sleeve 36 may also have a proximal portion 42 that is inserted into an annular inner groove 44 of the handpiece 10 and distal portion 46 that extends along the tip 26. The inner diameter of the outer sleeve 34 and the outer diameter of the inner sleeve 36 may be such to create an interference fit between the sleeves 34 and 36. The interference fit prevents relative movement and possible friction between the two sleeves 34 and 36.

A portion of the inner sleeve 36 may be separated from the tip 24 by an irrigation channel 48 that is in fluid communication with the irrigation port 28. The outer sleeve 34 may have an irrigation opening 50 that is in fluid communication with the irrigation channel 48. The tip 26 may extend through an opening 52 in the outer sleeve 34 in a manner that seals the sleeve 32 to the tip 26.

The sleeve 32 and tip 26 are typically inserted through an incision in a cornea 54 to perform a phacoemulsification procedure. The distal portion 46 of the inner sleeve 36 may have a length that is shorter than the distal portion 40 of the outer sleeve 36 so that the end of the irrigation sleeve 32 is flexible enough to be deflected during the phaco procedure.

The distance d that separates the proximal portion 42 of the inner sleeve 36 from the case 24 should be less than the distance D that separates the distal portion 46 of the inner sleeve 36 and tip 26 so that the proximal portion 42 engages the case 24 before the distal portion 46 makes contact with the tip 26. It is also desirable to provide an inner sleeve 36 stiffness that prevents a beam deflection of the sleeve 34 and contact with the tip 22 when maximum non-symmetrical forces are exerted by the cornea 54 onto the irrigation sleeve 32.

As shown in FIG. 4, the cornea may apply non-symmetric forces $F_3$ and $F_4$ ($F_3>F_4$) to the irrigation sleeve 30 which move the sleeve 32 toward the tip 26. The proximal portion 42 of the inner sleeve 36 makes contact with the outer case and prevents further movement of the sleeve 32 before the inner sleeve 36 makes contact with the tip. Coupling the proximal end of the rigid inner sleeve 36 to the case 24 thus increases the effective stiffness of the inner sleeve 36 and reduces the likelihood of contact between the sleeve 32 and tip 26 over irrigation sleeves of the prior art.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A sleeve for an ultrasonic handpiece, comprising:
   an outer sleeve which has a proximal portion and a distal portion that has an inner channel, said outer sleeve having a stiffness;
   an inner sleeve which has a proximal portion, and a distal portion that extends along said inner channel of said distal portion of said outer sleeve, said distal portion of said inner sleeve having a diameter that is smaller than a diameter of said proximal portion, said inner sleeve having a stiffness that is greater than a stiffness of said outer sleeve.

2. The sleeve of claim 1, wherein said inner sleeve is attached to said outer sleeve.

3. The sleeve of claim 1, wherein said distal portion of said inner sleeve has a length that is less than a length of said distal portion of said outer sleeve.

4. The sleeve of claim 1, wherein said inner sleeve is constructed from a plastic material and said outer sleeve is constructed from a rubber material.

5. The sleeve of claim 1, wherein said outer sleeve has an irrigation port.

6. The sleeve of claim 5, wherein said outer sleeve has a tip opening.

7. A medical handpiece, comprising:
   a case;
   a transducer located within said case;
   a tip that is coupled to said transducer;
   an outer sleeve which has a proximal portion that is coupled to said case and a distal portion that extends along said tip, said distal portion having an inner channel; and,
   an inner sleeve which has a proximal portion that is coupled to said case and a distal portion that extends along said inner channel of said distal portion of said outer sleeve.

8. The handpiece of claim 7, wherein said inner sleeve is attached to said outer sleeve.

9. The handpiece of claim 7, wherein said inner sleeve has a stiffness that is greater than a stiffness of said outer sleeve.

10. The handpiece of claim 9, wherein said inner sleeve is constructed from a plastic material and said outer sleeve is constructed from a rubber material.

11. The handpiece of claim 7, wherein said inner sleeve is separated from said tip by an irrigation channel.

12. The handpiece of claim 11, wherein said outer sleeve has an irrigation port that is in fluid communication with said irrigation channel.

13. The handpiece of claim 7, wherein said distal portion of said inner sleeve has a length that is less than a length of said distal portion of said outer sleeve.

14. The handpiece of claim 7, wherein tip extend through a tip opening of said outer sleeve.

15. A method for assembling a sleeve to a medical handpiece, comprising the steps of:
   coupling a proximal portion of an inner sleeve and a proximal portion of an outer sleeve to a case of the medical handpiece, wherein the inner sleeve has a distal portion that extends along an inner channel of a distal portion of the outer sleeve that extends along the tip.

* * * * *